(12) United States Patent
Hull et al.

(10) Patent No.: US 10,092,280 B2
(45) Date of Patent: *Oct. 9, 2018

(54) SPRAY APPLICATOR

(71) Applicant: Confluent Surgical, Inc., Plainsboro, NJ (US)

(72) Inventors: Les Hull, Attleboro, MA (US); Jason Fortier, Concord, MA (US)

(73) Assignee: Confluent Surgical, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/622,489

(22) Filed: Jun. 14, 2017

(65) Prior Publication Data
US 2017/0273675 A1    Sep. 28, 2017

Related U.S. Application Data

(60) Division of application No. 15/374,250, filed on Dec. 9, 2016, now Pat. No. 9,700,290, which is a
(Continued)

(51) Int. Cl.
*A61B 17/03* (2006.01)
*B05B 7/04* (2006.01)
(Continued)

(52) U.S. Cl.
CPC ..... *A61B 17/00491* (2013.01); *A61M 25/003* (2013.01); *A61M 25/0069* (2013.01);
(Continued)

(58) Field of Classification Search
CPC .... A61B 17/00491; A61B 2017/00292; A61B 2017/00495; A61B 2017/00522;
(Continued)

(56) References Cited

U.S. PATENT DOCUMENTS 3,054,563 A   9/1962 Steinen
3,112,074 A   11/1963 Green
(Continued)

FOREIGN PATENT DOCUMENTS

DE   29516077 U1   2/1997
EP   0689874 A1    1/1996
(Continued)

OTHER PUBLICATIONS

European Search Report for EP 09252161.6-1269 date of completion is Dec. 17, 2009 (3 pages).
(Continued)

*Primary Examiner* — Darren W Gorman
(74) *Attorney, Agent, or Firm* — Carter, DeLuca, Farrell & Schmidt, LLP

(57) ABSTRACT

A spray assembly for dispensing a mixture is provided. The spray assembly includes a connector configured for operable engagement with a first and second source of component and a source of pressurized fluid, and a tip operably connected to the connector. The tip includes an opening and defines a mixing chamber between the connector and the opening of the tip, and an insert member configured to be received in the mixing chamber. The insert member includes a plurality of radially extending slots on at least one end of the insert. The plurality of radially extending slots is configured to mix the first and second components prior to the mixture exiting the opening in the tip.

7 Claims, 6 Drawing Sheets

Related U.S. Application Data continuation of application No. 14/809,693, filed on Jul. 27, 2015, now Pat. No. 9,517,478, which is a continuation of application No. 14/143,605, filed on Dec. 30, 2013, now Pat. No. 9,101,946, which is a continuation of application No. 13/493,207, filed on Jun. 11, 2012, now Pat. No. 8,616,468, which is a continuation of application No. 12/555,435, filed on Sep. 8, 2009, now Pat. No. 8,210,453.

(60) Provisional application No. 61/096,345, filed on Sep. 12, 2008.

(51) Int. Cl.
   *B05B 7/10* (2006.01)
   *B05B 1/34* (2006.01)
   *A61B 17/00* (2006.01)
   *A61M 25/00* (2006.01)

(52) U.S. Cl.
   CPC ....... *A61M 25/0082* (2013.01); *B05B 1/3436* (2013.01); *B05B 7/0408* (2013.01); *B05B 7/0483* (2013.01); *B05B 7/10* (2013.01); *A61B 2017/00292* (2013.01); *A61B 2017/00495* (2013.01); *A61B 2017/00522* (2013.01); *A61M 2025/0073* (2013.01)

(58) Field of Classification Search
   CPC ............ A61M 25/003; A61M 25/0069; A61M 25/0082; A61M 2025/0073; A61M 35/00; A61M 35/003; B05B 1/3436; B05B 7/0408; B05B 7/0483; B05B 7/10
   See application file for complete search history.

(56) References Cited

U.S. PATENT DOCUMENTS

| | | |
|---|---|---|
| 3,828,980 A | 8/1974 | Creighton et al. |
| 4,040,420 A | 8/1977 | Speer |
| 4,359,049 A | 11/1982 | Redl et al. |
| 4,538,920 A | 9/1985 | Drake |
| 4,631,055 A | 12/1986 | Redl et al. |
| 4,735,616 A | 4/1988 | Eibl et al. |
| 4,753,536 A | 6/1988 | Spehar et al. |
| 4,767,026 A | 8/1988 | Keller et al. |
| 4,842,581 A | 6/1989 | Davis |
| 4,874,368 A * | 10/1989 | Miller .............. A61B 17/00491 222/137 |
| 4,978,336 A | 12/1990 | Capozzi et al. |
| 4,979,942 A | 12/1990 | Wolf et al. |
| 5,049,135 A | 9/1991 | Davis |
| 5,104,375 A | 4/1992 | Wolf et al. |
| 5,116,315 A * | 5/1992 | Capozzi ........... A61B 17/00491 222/137 |
| 5,249,709 A | 10/1993 | Duckworth et al. |
| 5,249,862 A | 10/1993 | Herold et al. |
| 5,328,462 A | 7/1994 | Fischer |
| 5,333,760 A | 8/1994 | Simmen |
| 5,413,253 A | 5/1995 | Simmen |
| 5,445,614 A | 8/1995 | Haber et al. |
| 5,474,540 A | 12/1995 | Miller et al. |
| 5,605,255 A * | 2/1997 | Reidel .............. A61B 17/00491 222/137 |
| 5,641,125 A | 6/1997 | Martin et al. |
| 5,643,206 A | 7/1997 | Fischer |
| 5,665,066 A | 9/1997 | Fischer |
| 5,665,067 A * | 9/1997 | Linder .............. A61B 17/00491 604/191 |
| 5,740,965 A * | 4/1998 | Miyagi ............ A61B 17/00491 239/423 |
| 5,810,885 A * | 9/1998 | Zinger ............. A61M 25/0021 604/197 |
| 5,814,022 A | 9/1998 | Antanavich et al. |
| 5,819,988 A | 10/1998 | Sawhney et al. |
| RE36,235 E | 6/1999 | Keller et al. |
| 6,047,861 A | 4/2000 | Vidal et al. |
| 6,065,645 A | 5/2000 | Sawhney et al. |
| 6,132,396 A | 10/2000 | Antanavich et al. |
| 6,161,730 A | 12/2000 | Heusser et al. |
| 6,179,862 B1 * | 1/2001 | Sawhney .......... A61B 17/00491 604/197 |
| 6,328,229 B1 | 12/2001 | Duronio et al. |
| 6,398,761 B1 | 6/2002 | Bills et al. |
| 6,527,749 B1 | 3/2003 | Roby et al. |
| 6,585,696 B2 | 7/2003 | Petersen et al. |
| 6,648,852 B2 | 11/2003 | Wirt et al. |
| 6,698,622 B2 | 3/2004 | Sawhney et al. |
| 6,705,756 B2 | 3/2004 | Botrie et al. |
| 6,752,292 B2 | 6/2004 | Van Herpen |
| 6,769,574 B1 | 8/2004 | Keller |
| 6,773,414 B2 | 8/2004 | Ljungquist |
| 6,783,514 B2 | 8/2004 | Tovey et al. |
| 6,802,822 B1 * | 10/2004 | Dodge ............. A61B 17/00491 604/82 |
| 6,820,766 B2 | 11/2004 | Keller et al. |
| 6,835,186 B1 | 12/2004 | Pennington et al. |
| 6,852,099 B2 | 2/2005 | Redl et al. |
| 6,884,232 B1 * | 4/2005 | Hagmann ........ A61B 17/00491 604/191 |
| 6,921,380 B1 | 7/2005 | Epstein et al. |
| 6,921,381 B2 | 7/2005 | Spero et al. |
| 6,994,686 B2 | 2/2006 | Cruise et al. |
| 7,037,289 B2 | 5/2006 | Dodge et al. |
| 7,124,574 B2 | 10/2006 | Horn et al. |
| 7,124,914 B2 | 10/2006 | Foster et al. |
| 7,128,278 B2 | 10/2006 | Archambeau et al. |
| 7,131,597 B2 | 11/2006 | Scattergood |
| 7,140,558 B2 | 11/2006 | McCracken et al. |
| 7,140,560 B2 | 11/2006 | Stotts et al. |
| 7,140,797 B2 | 11/2006 | Hunter et al. |
| 7,152,396 B2 | 12/2006 | Cheng |
| 7,152,813 B2 | 12/2006 | Chen |
| 7,156,835 B2 | 1/2007 | Epstein |
| 7,159,796 B2 | 1/2007 | Yquel |
| 7,164,133 B2 | 1/2007 | Hjertman et al. |
| 7,172,733 B2 | 2/2007 | Gauthier et al. |
| 7,178,742 B2 | 2/2007 | Mellentine et al. |
| 7,178,743 B2 | 2/2007 | Clarke, III et al. |
| 7,178,744 B2 | 2/2007 | Tapphorn et al. |
| 7,182,279 B2 | 2/2007 | Wang |
| 7,185,829 B2 | 3/2007 | Sundholm |
| 7,191,917 B2 | 3/2007 | Brinz et al. |
| 7,191,959 B2 | 3/2007 | Kutay et al. |
| 7,195,135 B1 | 3/2007 | Garcia et al. |
| 7,195,180 B2 | 3/2007 | Lee |
| 7,201,336 B2 | 4/2007 | Blette et al. |
| 7,207,969 B2 | 4/2007 | Epstein et al. |
| 7,217,254 B2 | 5/2007 | Kirwan et al. |
| 7,222,752 B2 | 5/2007 | Ponton |
| 7,223,426 B2 | 5/2007 | Cheng et al. |
| 7,225,999 B2 | 6/2007 | Foianini et al. |
| 7,232,080 B2 | 6/2007 | Kutay et al. |
| 7,232,082 B2 | 6/2007 | Muhlhausen et al. |
| 7,237,693 B2 | 7/2007 | Brennan et al. |
| 7,237,726 B2 | 7/2007 | Yu |
| 7,244,248 B2 | 7/2007 | Azzolini |
| 7,246,758 B2 | 7/2007 | Wang |
| 7,252,243 B2 | 8/2007 | Bjorn et al. |
| 7,252,247 B2 | 8/2007 | Holm et al. |
| 7,264,179 B2 | 9/2007 | Robbins |
| 7,267,288 B2 | 9/2007 | Wheeler, Jr. et al. |
| 7,270,654 B2 | 9/2007 | Griego et al. |
| 7,275,699 B2 | 10/2007 | Schmidt |
| 7,278,985 B2 | 10/2007 | Agerup |
| 9,101,946 B2 | 8/2015 | Hull et al. |
| 9,517,478 B2 | 12/2016 | Hull et al. |
| 9,700,290 B2 | 7/2017 | Hull et al. |
| 2002/0104851 A1 | 8/2002 | Parise |
| 2002/0165483 A1 | 11/2002 | Miller et al. |
| 2003/0069537 A1 | 4/2003 | Spero et al. |
| 2003/0183653 A1 | 10/2003 | Bills |
| 2003/0209612 A1 | 11/2003 | Hahnen |

(56) References Cited

U.S. PATENT DOCUMENTS

| | | |
|---|---|---|
| 2005/0096588 A1 | 5/2005 | Hagmann et al. |
| 2006/0071025 A1 | 4/2006 | Crews |
| 2006/0189944 A1* | 8/2006 | Campbell ........ A61B 17/00491 604/191 |
| 2007/0005007 A1 | 1/2007 | Hoogenakker et al. |
| 2007/0131795 A1* | 6/2007 | Abbate ............ A61B 17/00491 239/400 |
| 2008/0121738 A1* | 5/2008 | Togashi .................. B05B 1/341 239/406 |
| 2009/0199848 A1 | 8/2009 | Sharratt |

FOREIGN PATENT DOCUMENTS

| | | | |
|---|---|---|---|
| JP | 332959 | 3/1991 | |
| WO | 0205898 A1 | 1/2002 | |
| WO | WO 0205898 A1 * | 1/2002 | ....... A61B 17/00491 |

OTHER PUBLICATIONS

*Confluent Surgical, Inc.* v. *Hyperbranch Medical Technology, Inc.*, Hyperbranch Medical Technology, Inc.'s Preliminary Initial Invalidity Contentions, Civil Action No. 17-688 (LPS)(CJB) dated Jan. 29, 2018.

*Confluent Surgical, Inc.* v. *Hyperbranch Medical Technology, Inc.*, Defendant's Answer and Counterclaims to Second Amended Complaint for Patent Infringement, Civil Action No. 17-688 (LPS)(CJB) dated Dec. 11, 2017.

\* cited by examiner

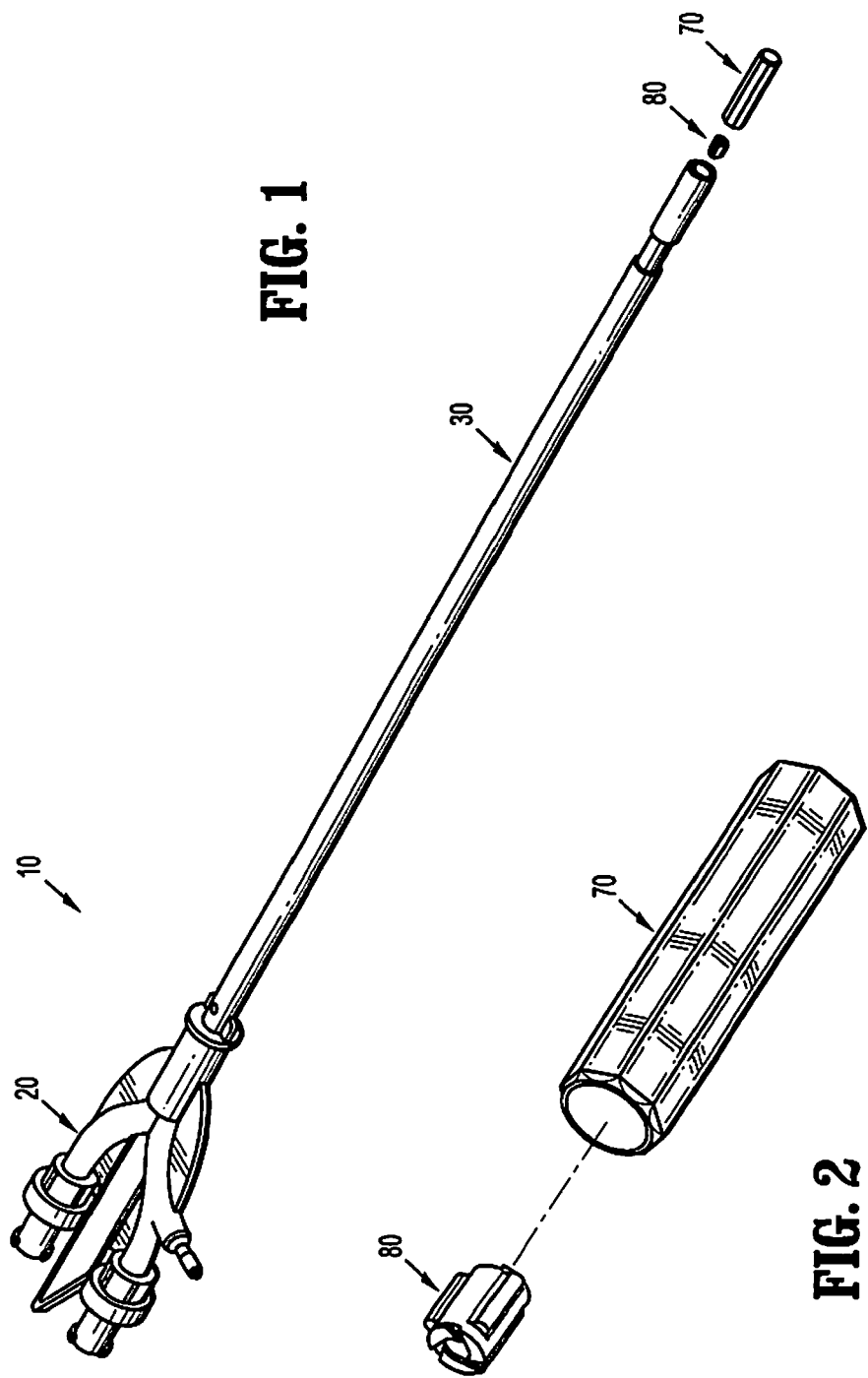

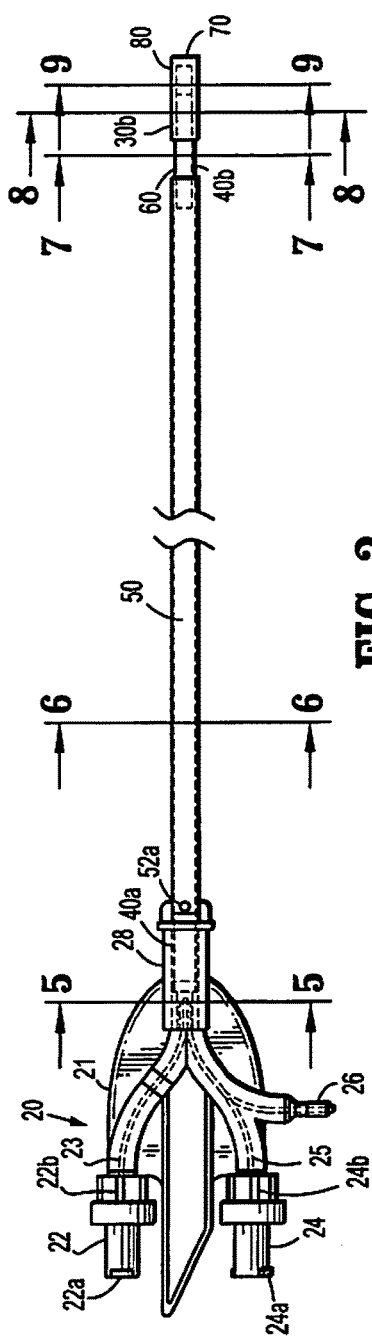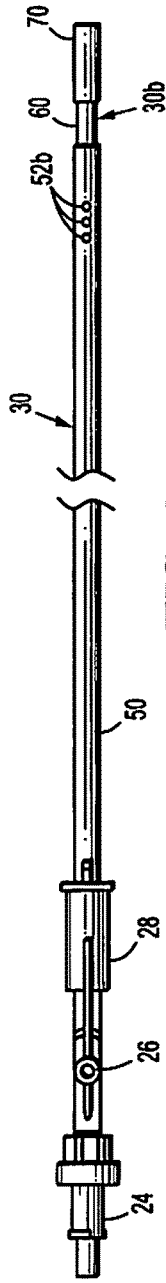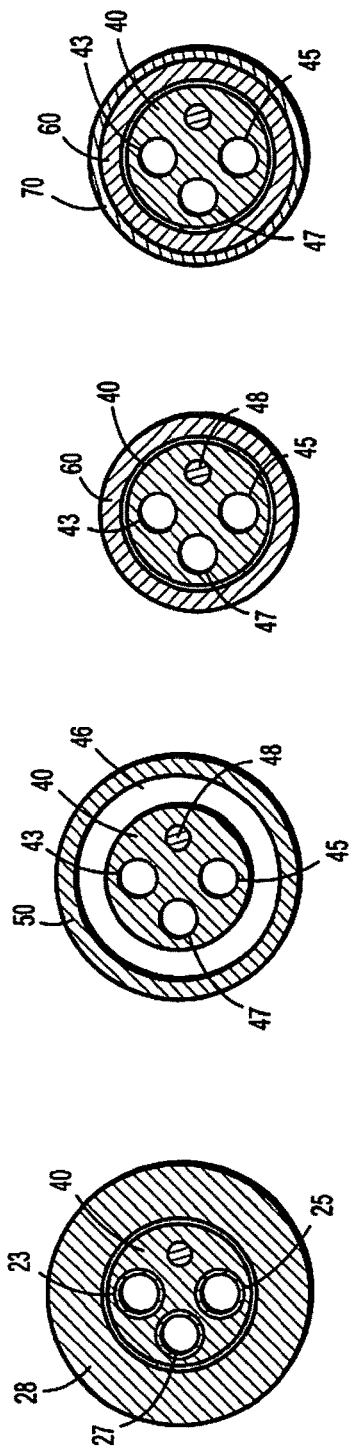

SPRAY APPLICATOR

CROSS-REFERENCE TO RELATED APPLICATIONS

This application is a divisional of U.S. application Ser. No. 15/374,250 filed on Dec. 9, 2016, which is a continuation of U.S. application Ser. No. 14/809,693 filed on Jul. 27, 2015, now U.S. Pat. No. 9,517,478, which is a continuation of U.S. application Ser. No. 14/143,605 filed on Dec. 30, 2013, now U.S. Pat. No. 9,101,946, which is a continuation of U.S. application Ser. No. 13/493,207 filed on Jun. 11, 2012, now U.S. Pat. No. 8,616,468, which is a continuation of U.S. application Ser. No. 12/555,435 filed on Sep. 8, 2009, now U.S. Pat. No. 8,210,453, which claims the benefit of and priority to U.S. Provisional Patent Application No. 61/096,345, filed Sep. 12, 2008, the entire disclosure of each application is incorporated by reference herein.

BACKGROUND

Technical Field

The present disclosure relates to spray applicators and methods of mixing two or more components. More particularly, the present disclosure relates to a spray assembly for mixing and applying a bioadhesive.

Background of Related Art

Polymers and other synthetic materials are currently being developed for use in internal and external wound closure. "Bioadhesives" are known in the art, as are various methods for applying the bioadhesive. Bioadhesives offer many significant advantages over conventional wound closure methods, i.e., using sutures, staples, clips or other suitable mechanical fasteners. Bioadhesives are faster and simpler to apply and have a tendency to promote quicker wound healing with less scarring.

Most bioadhesives are composed of components that have a tendency to immediately activate and in some instances, rapidly polymerize when combined with one another. Because of this immediate activation and/or rapid polymerization of the bioadhesive, the components comprising the bioadhesive may not be combined until immediately prior to application.

The increased use of endoscopic surgery for even some of the most complex procedures has presented a need for an applicator configured to apply a bioadhesive through an endoscopic port.

SUMMARY

Provided is a spray assembly for dispensing a mixture. The spray assembly includes a connector configured for operable engagement with a first and a second source of component and a source of pressurized fluid, a tip operably connected to the connector, the tip including an opening and defining a mixing chamber between the distal end of the elongated member and the opening of the tip, and an insert member configured to be received in the mixing chamber, the insert member including a plurality of radially extending slots on at least one end of the insert, the plurality of radially extending slots being configured to mix the first and second components prior to the combination exiting the opening in the tip. The spray assembly may further include an elongated member extending between the connector and the tip, the elongated member having at least a first lumen configured for fluid communication with the first source of component, a second lumen configured for fluid communication with the second source of component, and a third lumen configured for fluid communication with the source of pressurized fluid. The spray assembly may further include a first and a second source of component. The insert member of the spray assembly may include three slots.

An alternate embodiment of a spray assembly for dispensing a mixture is also provided. The spray assembly includes a connector configured for operable engagement with a first and a second source of component and a source of pressurized fluid, and a tip operably connected to the connector, the tip including an opening and defining a mixing chamber between the distal end of the elongated member and the opening of the tip, the distal end of the mixing chamber including a plurality of radially extending slots formed about the opening, the plurality of radially extending slots being configured to mix the first and second components prior to the combination exiting the opening in the tip. The spray assembly may further include an elongated member extending between the connector and the tip, the elongated member having at least a first lumen configured for fluid communication with the first source of component, a second lumen configured for fluid communication with the second source of component, and a third lumen configured for fluid communication with the source of pressurized fluid,

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 1 is an exploded perspective view of a spray assembly according to the present disclosure;

FIG. 2 is an enlarged perspective view of the insert and applicator tip of the spray assembly of FIG. 1;

FIG. 3 is a top view of the spray assembly of FIG. 1;

FIG. 4 is a side view of the spray assembly of FIGS. 1 and 3;

FIG. 5 is a cross-sectional end view taken along line 5-5 of FIG. 3;

FIG. 6 is a cross-sectional end view taken along line 6-6 of FIG. 3;

FIG. 7 is a cross-sectional end view taken along line 7-7 of FIG. 3;

FIG. 8 is a cross-sectional end view taken along line 8-8 of FIG. 3;

DETAILED DESCRIPTION

Figure 9:
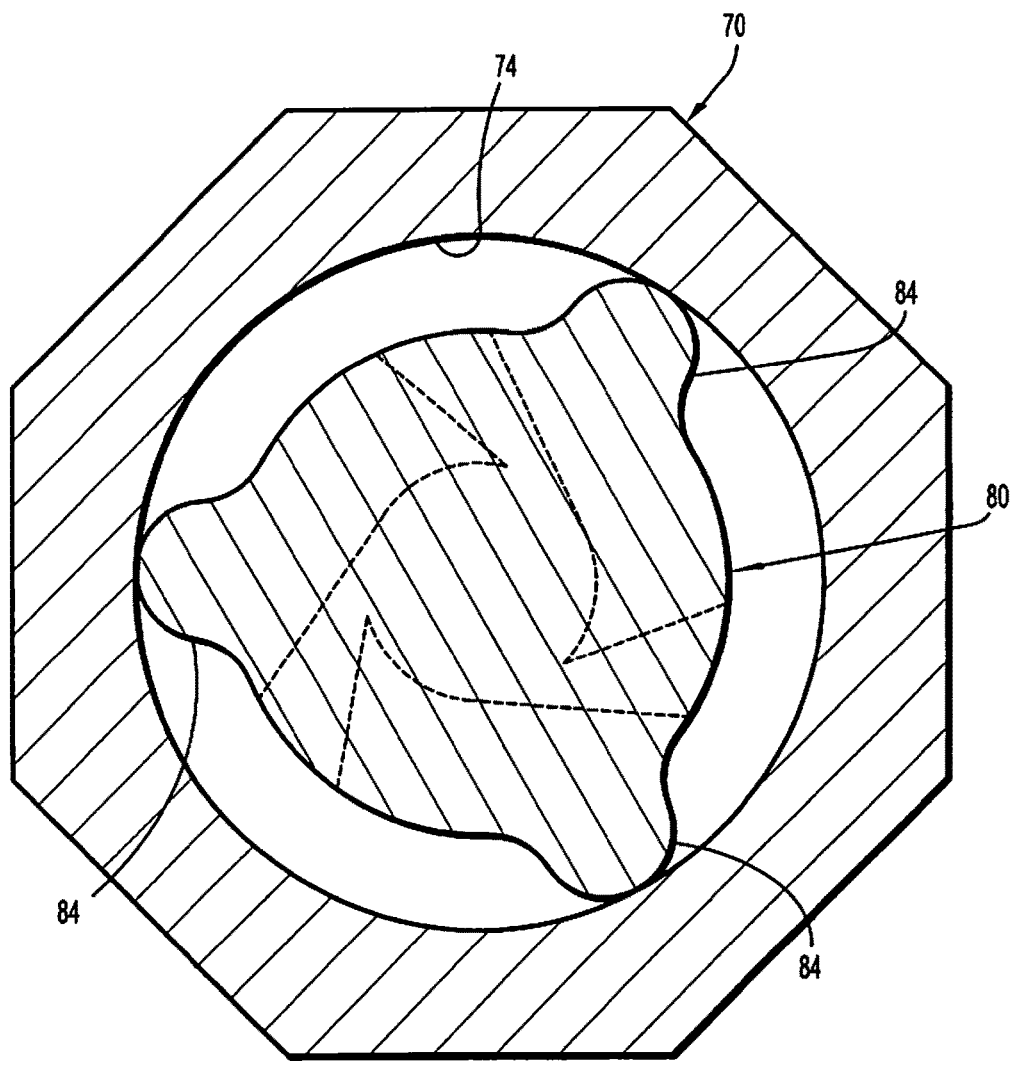
FIG. 9 is a cross-sectional end view taken along line 9-9 of FIG. 3.
Figure 10:
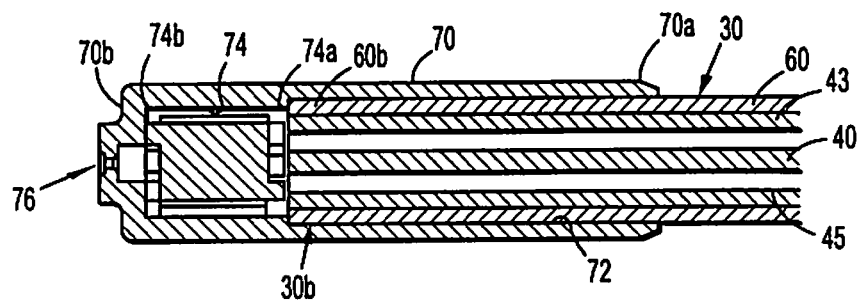
FIG. 10 is a cross-sectional side view of the distal end of the spray assembly of FIGS. 1 and 3.
Figure 11:
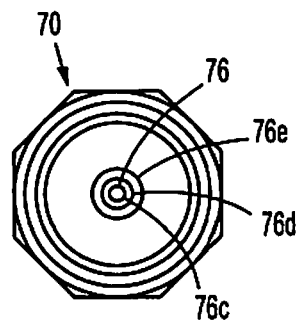
FIG. 11 is a distal end view of the spray assembly of FIGS. 1 and 3.

As shown below in FIGS. 1 and 2, an embodiment of a spray assembly, i.e., a laparoscopic spray assembly, in accordance with the present disclosure is shown generally as spray assembly 10. Spray assembly 10 includes a Y-connector 20, an elongated body portion 30 extending distally from Y-connector 20, and an applicator tip 70 mounted on a distal end of elongated body portion 30. Spray assembly 10 further includes an insert member 80 received between a distal end of elongated body portion 30 and a distal end of applicator tip 70.

Referring now to FIGS. 3 and 4, Y-connector 20 defines a substantially Y-shaped member 21 including first and second proximal extensions 22, 24, an air supply port 26, and a collar 28. Although shown in a substantially planar arrangement, first and second proximal extensions 22, 24 and air supply port 26 may be arranged in any manner. Each of first and second proximal extensions 22, 24 includes a tab 22a, 24a, respectively, for operable engagement with a bayonet coupling (not shown) found on standard syringes. It is envisioned, however, that first and second extensions 22, 24 may configured for coupling with any source of fluid in any manner. First and second proximal extensions 22, 24 may further include component check valves 22b, 24b or other means for selectively regulating the flow from first and second proximal extensions 22, 24 and prevent backflow. First and second component channels 23, 25 extend between first and second proximal extensions 22, 24 and collar 28. An air channel 27 extends between air supply port 26 and collar 28. First and second component channels 23, 25 and/or air channel 27 may be configured to include anti-backflow mechanisms. As will be discussed in further detail below, collar 28 maintains first and second component channels 23, 25 and air supply port 26 in fluid communication with a first and second component lumen 43, 45 and an air lumen 47 (FIG. 6), respectively, formed in inner multi-lumen shaft 40 of elongated body portion 30.

With reference to FIGS. 5-9, elongated body portion 30 of spray assembly 10 includes an inner multi-lumen shaft 40, an outer sleeve 50 (FIG. 6) surrounding inner shaft 40 and a transition member 60 extending distally from outer sleeve 50 about inner shaft 40. In one embodiment, outer sleeve 50 is rigid while inner multi-lumen shaft 40 and transition member 60 are flexible. Inner shaft 40 and outer sleeve 50 are securely affixed to Y-connector 20 and include a vent lumen 46 (FIG. 6) therebetween. Outer sleeve 50 includes a proximal vent or opening 52a (FIG. 3) and a plurality of distal vents or openings 52b (FIG. 4). Proximal and distal vents 52a, 52b may be of any number, size, configuration and arrangement. Distal vents 52b are in fluid communication with proximal vent 52a via vent lumen 46.

As discussed above, proximal end 40a of inner shaft 40 engages Y-connector 20 such that first and second component lumen 43, 45 and air lumen 47 align with first and second component channels 23, 25 and air lumen 27 (FIG. 5), respectively. In one embodiment, collar 28 of Y-connector 20 is molded directly around the proximal end of elongated body portion 30. Alternatively, elongated body portion 30 may be selectively engagable with collar 28 such that elongated body portion 30 and collar 28 may be separated and one of the two replaced. In yet another embodiment, elongated body portion 30 may be securely affixed to collar 28 using adhesive, sonic welding or other suitable method. Inner shaft 40 may further includes a wire or other formable material 48 configured to maintain elongated body portion 30 distal of outer sleeve 50 in a desired straight, bent or flexed condition. A proximal end of transition member 60 is received within vent lumen 46 between outer sleeve 50 and inner shaft 40.

Transition member 60 extends from outer sleeve 50 about inner shaft 40 and may be of any length. Transition member 60 may include a flexible material, thereby permitting inner shaft 40 to be bent and formed. In an alternate embodiment, transition member 60 may be integrally formed with inner shaft 40. In this manner, the portion of inner shaft extending beyond the distal end of outer sleeve 50 would have a larger diameter than the portion of inner shaft 40 within outer sleeve 50. A distal end 60b of transition member 60 may include a groove, threading or other configuration to selectively receive a applicator tip 70.

Turning now to FIGS. 8-12, applicator tip 70 is a tubular member having an open proximal end 70a and a substantially closed distal end 70b. Applicator tip 70 defines an engagement portion 72, a mixing chamber 74 and an outlet 76. Engagement portion 72 is configured to selectively engage distal end 60b of transition member 60. Engagement portion 72 may include grooves, tabs or other configurations corresponding to tabs, grooves and other configurations formed on the distal end of transition member 60. Engagement portion 72 may otherwise be configured to more securely engage the distal end of transition member 60.

Figure 12:
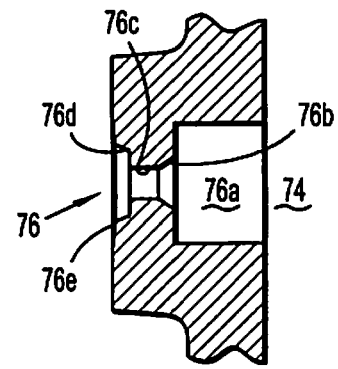
FIG. 12 is an enlarged cross-sectional side view of the distal end of the applicator tip of FIG. 11.

Mixing chamber 74 is an annular cavity in fluid communication with first and second component lumen 43, 45 and air lumen 47 (FIG. 5) of inner shaft 40. Mixing chamber 74 includes a proximal end 74a and outlet 76 on a distal end 74b. Mixing chamber 74 is sized to receive insert 80 immediately adjacent to or flush against distal end 74b. Outlet 76 is formed in distal end 70b of applicator tip 70. Outlet 76 is configured to atomize the combined first and second components. With reference to FIG. 12, in one embodiment, outlet 76, described distally from mixing chamber 74, includes a first annular portion 76a, a first tapered portion 76b, a second annular portion 76c, a second tapered portion 76d and a recessed portion 76e. Alternative configurations for atomizing a solution are known and have been envisioned for use with spray assembly 10.

Turning now to FIGS. 13A-13D, insert 80 is defined by a substantially annular body 81 having proximal and distal ends 80a, 80b. Proximal and distal ends 80a, 80b are substantial mirror images of one another. Proximal and distal ends 80a, 80b each define substantially annular recesses 81a, 81b, respectively. In one embodiment, each of proximal and distal ends 80a, 80b further includes a set of slots 82a, 82b. Slots 82a, 82b are included in both proximal and distal ends 80a, 80b in order to simplify the assembly process of spray assembly 10. It is envisioned, however, that only one end of insert 80 may include slots 82. Slots 82a, 82b are equally spaced about respective proximal and distal ends 80a, 80b. Although shown including three slots 82a, 82b, an insert 80 including two or more slots has been envisioned. Each of slots 82a, 82b defines an opening angling outwardly between a line tangent to recesses 81a, 81b, respectively, and a degrees counter-clockwise from the tangent line. In one embodiment, a is equal to twenty degrees (20°). Slots 82a formed on proximal end 80a are radial offset from slots 82b formed on distal end 80b. Insert 80 includes three spacers 84 equally spaced about and extending longitudinally along annular body 81. As will be discussed in further detail below, spacers 84 align and maintain insert 80 within mixing chamber 74. It is envisioned that insert 80 may include more or less than three spacers 84.

With reference back to FIG. 10, applicator tip 70 of applicator assembly 10 is shown in an assembled condition. Insert 80 is received immediately adjacent to, or flush against, the distal end of mixing chamber 74 of applicator tip 70. Spacers 84 formed on annular body 81 maintain insert 80 radially centered within distal end 74b of mixing chamber 74. Distal end 60b of transition member 60 is received within engagement portion 72 of applicator tip 70. Mixing chamber 74 is sized such that distal end 60b of transition member 60 and distal end 40b of inner shaft 40 abut insert 80.

In operation, first and second sources of component (not shown) are connected with first and second proximal extensions 22, 24, respectively, formed in Y-connector 20. The first and second components are ejected into first and second component channels 23, 25, respectively, and travel through first and second component lumen 43, 45, respectively formed in inner shaft 40. Air or other gaseous fluid is provided to spray assembly 10 through air supply port 26. In one embodiment, the gas supplied through air supply port 26 is a combination of oxygen ($O_2$) and carbon dioxide ($CO_2$); however, the use of other gases, alone or in combination, is envisioned. The air flows into air channel 27 and through air lumen 47 formed in inner shaft 47. The first and second components and the air provided through Y-connector 20 exit first and second lumen 43, 45 and air lumen 47, respectively, at distal end 40b (FIG. 3) of inner shaft 40.

The first and second components and the air exiting inner shaft 40 encounter proximal end 80a of insert 80. The components and air initially meet as the components and air are forced around insert 80 through the space created by spacers 84 between mixing chamber 74 and annular body 81. When the component/gas combination reaches distal end 80b of insert 80, the combination is further mixed by the turbulent or swirling motion created by slots 82b as the mixture enters recess 81b. The swirling fluid is then ejected from applicator tip 70 through outlet 76 in the form of a cone spray. In the event that distal end 80b of insert 80 is not flush against the distal end of chamber 74, the mixture would not swirl through slots 82b thereby resulting in a jet-like spray through outlet 76. Insert 80 is forced against and maintained flush with the distal end of mixing chamber 74 because of the contact between spacers 84 on annular body 81 and mixing chamber 74. The force of the components and air against insert 80 also maintains insert 80 flush against the distal end of applicator tip 70.

Figure 14:
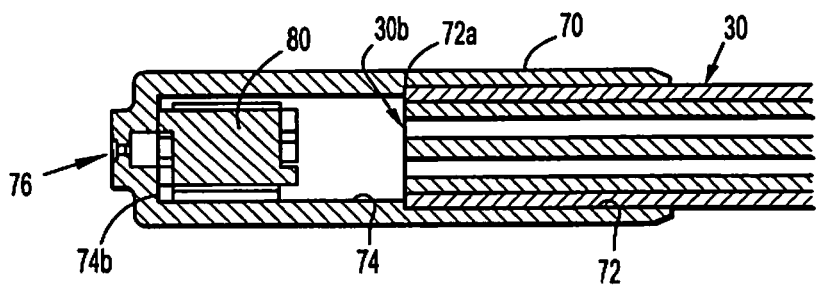
FIG. 14 is an alternate embodiment of a spray assembly according to the present disclosure.
Figure 13C:
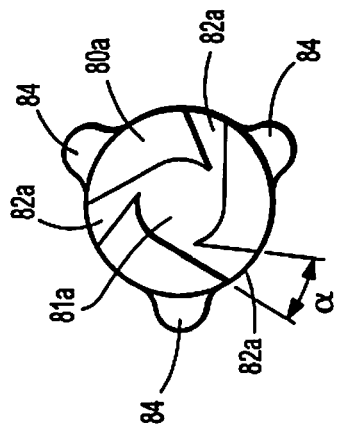
FIGS. 13A-D are side view (FIG. 13A), distal end view (FIG. 13B), proximal end view (FIG. 13C), and cross-sectional top view taken along line 13D-13D of FIG. 13A (FIG. 13D) of the insert of FIG. 2.
Figure 13A:
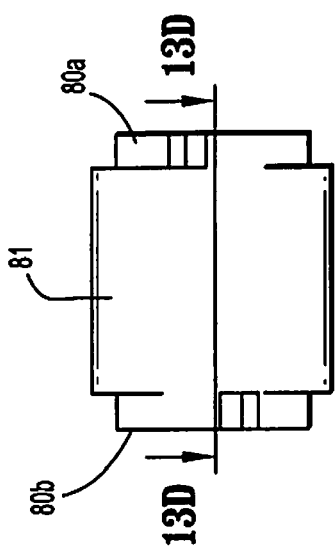
Figure 13D:
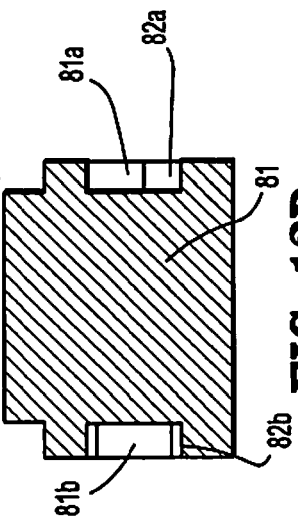
Figure 13B:
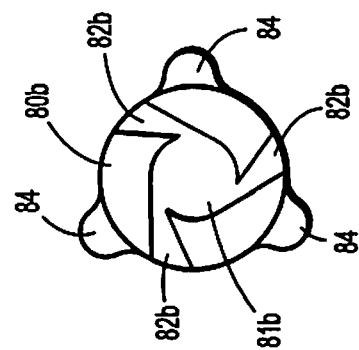

With reference to FIG. 14, in an alternate embodiment of applicator tip 70, mixing chamber 74 is sized such that insert 80 is longitudinally spaced from distal end 30b of elongated body member 30, thereby forming a cavity for the initial mixing of first and second components prior to encountering insert 80. In one embodiment, applicator tip 70 includes a lip or ridge 72a, to prevent engagement of elongated body portion 30 with insert 80. The first and second components and gas are first combined within proximal end 74a of mixing chamber 74 as the first and second components exit distal end 40b of inner shaft 40. The combined first and second components form a mixture that next encounters proximal end 80a of insert 80. The mixture is forced around insert 80 through the space created by spacers 84 between mixing chamber 74 and annular body 81. When the mixture reaches distal end 80b of insert 80, the mixture is further mixed and swirled by slots 82b as the mixture enters recess 81b. The swirling fluid is then ejected from applicator tip 70 through outlet 76 in the form of a cone spray. As discussed above, in the event that distal end 80b of insert 80 is not flush against distal end 74b of chamber 74, the mixture would not swirl through slots 82b thereby resulting in a jet-like spray. Insert 80 is maintained flush against distal end of mixing chamber 74 by the force of the first and second component and gas flowing against proximal end 80a thereof. Insert 80 is also forced against and maintained flush with distal end of mixing chamber 74 because of contact between spacers 84 on annular body 81 and mixing chamber 74.

Figure 15:
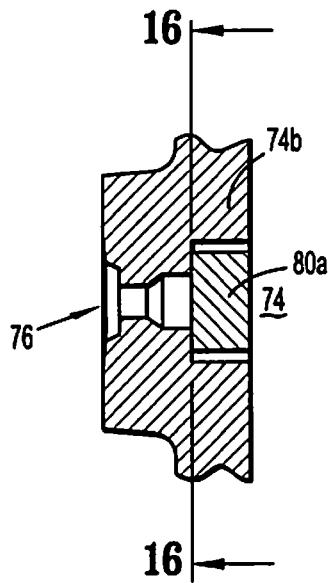
FIG. 15 is an enlarged cross-sectional side view of the distal end of an alternate embodiment of an applicator tip according to the present disclosure.
Figure 16:
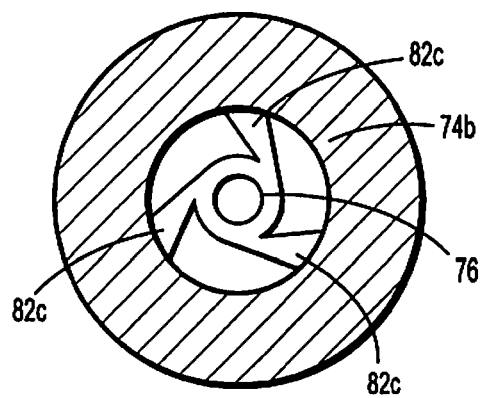
FIG. 16 is an enlarged cross-sectional end view of the applicator tip of FIG. 14 taken along line 16-16 OF FIG. 15.

Turning now to FIGS. 15 and 16, distal end 74b of mixing chamber 74 of applicator tip 70 may alternately be configured to include radially extending slots 82c formed about opening 76. Slots 82c are similar in form and function to slots 82a, 82b formed in proximal and distal ends 80a, 80b, respectively of insert 80. As with slots 82a, 82b described hereinabove, slots 82c may be of any number size, configuration or orientation. In a spray assembly utilizing mixing chamber 74 having slots 82c, insert 80a replaces insert 80. Insert 80a is configured to be retained within mixing chamber 74 in a manner similar to insert 80, however, insert 80a does not include slots 82a, 82b. Applicator tip 70, may alternatively be configured to direct the first and second components into slots 82c without insert 80a.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. For example, it is envisioned that the spray assembly of the present disclosure may be configured to mix and dispense a mixture including more than two components. It is further envisioned that the spray assembly may be configured for connection with more than one gas supply source.

What is claimed is:

1. A method of dispensing a mixture, the method comprising:
    dispersing a first component from a first source of component and a second component from a second source of component into a mixing chamber of a tip assembly;
    dispersing pressurized air from a source of pressurized air into the mixing chamber;
    continuing to disperse the first and second components from the respective first and second sources of component and the pressurized air from the source of pressurized air into the mixing chamber, the tip assembly including an insert member defining a plurality of slots on proximal and distal ends thereof for mixing the first and second components to form a mixture;
    positioning an outlet of the tip assembly in proximity to a target location; and
    dispensing the mixture of the first and second components at the target location through the tip assembly.

2. The method of claim 1, wherein positioning the outlet of the tip assembly includes positioning the tip assembly in a body cavity of a patient.

3. The method of claim 1, wherein dispersing the first and second components and dispersing the pressurized air are performed simultaneously.

4. The method of claim 1, wherein dispensing the mixture includes dispensing the mixture in a spray cone.

5. The method of claim 1, wherein positioning the outlet of the tip assembly includes bending an elongated body portion disposed proximal of the tip assembly.

6. The method of claim 1, wherein dispersing pressurized air from the source of pressurized air includes coupling the source of pressurized air to a connector.

7. The method of claim 1, wherein dispersing the first component from the first source of component and the second component from the second source of component includes coupling the first and second sources of component to a connector.

\* \* \* \* \*